(12) United States Patent
Gysland

(10) Patent No.: US 8,757,169 B2
(45) Date of Patent: Jun. 24, 2014

(54) ELECTRONIC CIGARETTE REFILLING APPARATUS

(76) Inventor: David Gysland, Sauk Rapids, MN (US)

( * ) Notice: Subject to any disclaimer, the term of this patent is extended or adjusted under 35 U.S.C. 154(b) by 846 days.

(21) Appl. No.: 12/980,785

(22) Filed: Dec. 29, 2010

(65) Prior Publication Data

US 2012/0167906 A1    Jul. 5, 2012

(51) Int. Cl.
A24F 47/00 (2006.01)
(52) U.S. Cl.
USPC .......................................... 131/271; 131/270
(58) Field of Classification Search
None
See application file for complete search history.

(56) References Cited

U.S. PATENT DOCUMENTS

| 4,592,348 A | 6/1986 | Waters et al. |
| 2005/0016550 A1 | 1/2005 | Katase |
| 2006/0196518 A1 | 9/2006 | Hon |
| 2007/0267031 A1* | 11/2007 | Hon ............................. 131/273 |
| 2008/0230052 A1 | 9/2008 | Montaser |
| 2008/0247892 A1* | 10/2008 | Kawasumi .................... 417/476 |
| 2008/0257367 A1 | 10/2008 | Paterno et al. |
| 2008/0276947 A1 | 11/2008 | Martzel |
| 2009/0095311 A1 | 4/2009 | Han |
| 2009/0126745 A1 | 5/2009 | Hon |
| 2010/0031968 A1* | 2/2010 | Sheikh et al. ................. 131/347 |
| 2010/0200008 A1 | 8/2010 | Taieb |
| 2010/0242974 A1 | 9/2010 | Pan |

* cited by examiner

*Primary Examiner* — Michael J Felton
(74) *Attorney, Agent, or Firm* — Mitchell A. Rossman; Terra Nova Patent Law, PLLC.

(57) ABSTRACT

An electronic cigarette including an atomizer, a cartridge, a mouthpiece, a power switch, and an electronic cigarette refilling apparatus for use therein is disclosed. A method of dispensing a liquid into an electronic cigarette and a method of inhaling a vapor from an electronic cigarette are also disclosed.

12 Claims, 11 Drawing Sheets

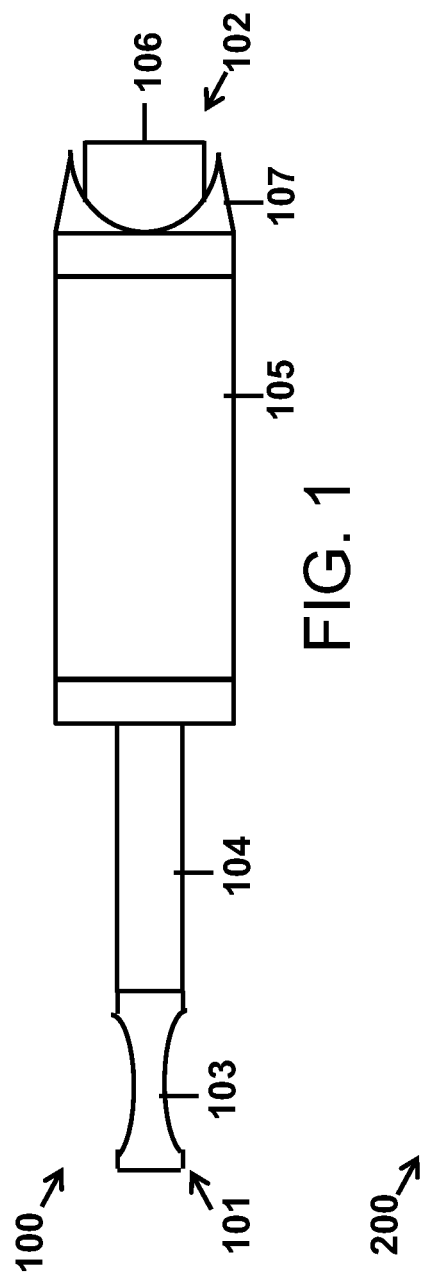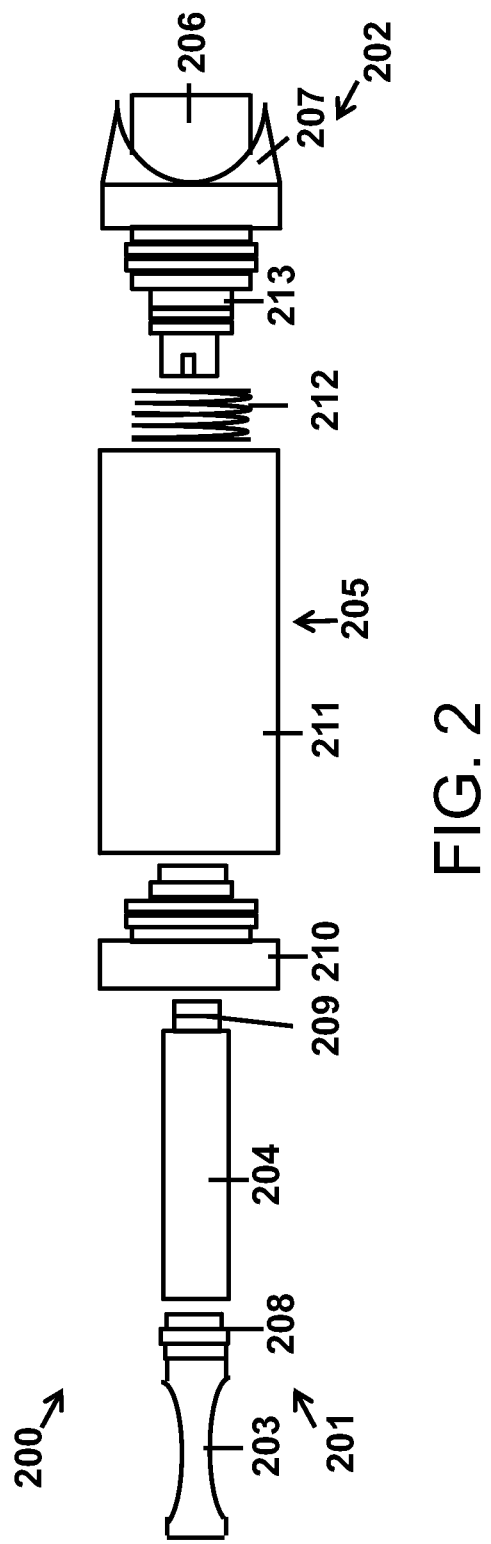

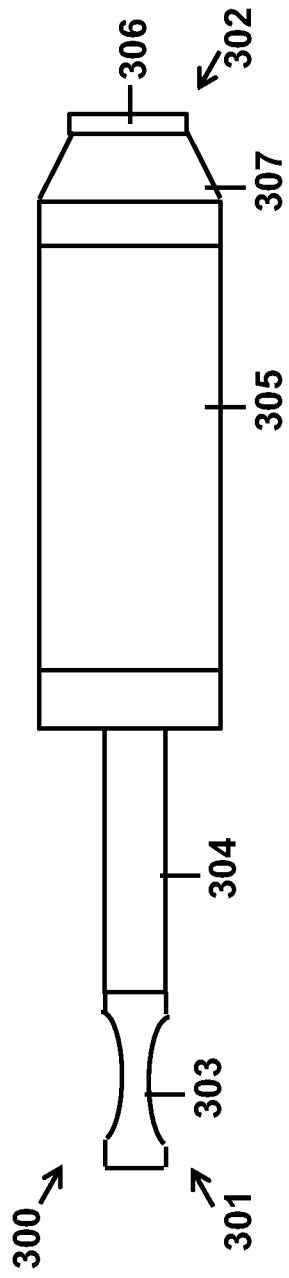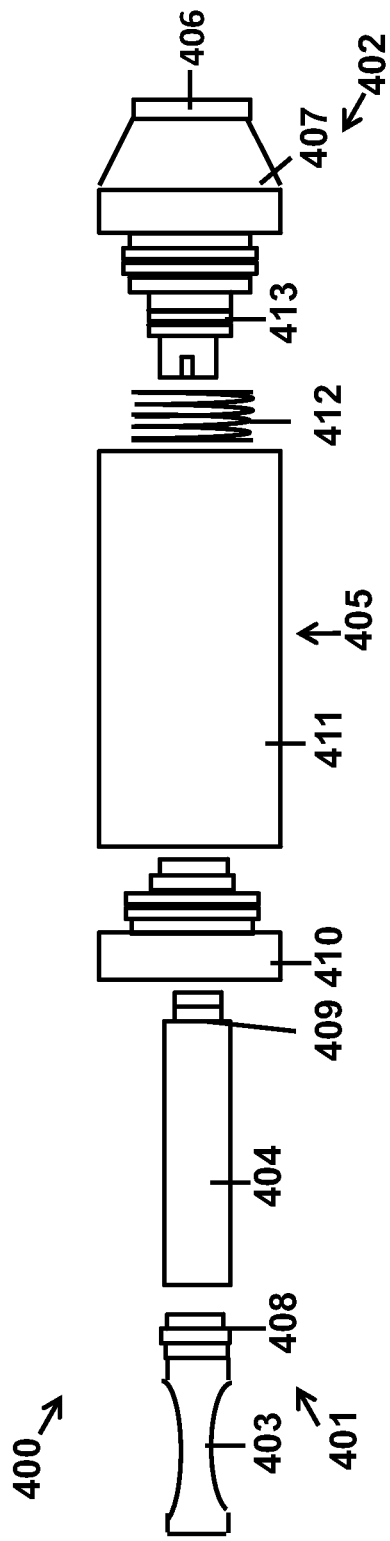

ELECTRONIC CIGARETTE REFILLING APPARATUS

BACKGROUND OF THE INVENTION

Conventional smoking devices, including cigarettes, cigars and pipes, are associated with a variety of problems. These devices burn tobacco, which creates a significant fire risk in, for example, cars, home, offices, factories, mines, and in many other environments. Further, the burning of tobacco creates tar, which is believed to be cause health problems, including, for example, cancer. In addition, inhalation of second-hand smoke by third-parties increases the health risk of the third-parties developing such conditions.

For those and other reasons, many facilities have banned smoking indoors and on their properties. However, many smokers enjoy regular smoking, and may experience unpleasant psychological or even physiological withdrawal symptoms if they are unable to smoke frequently.

To address that issue, smoking-substitute devices have been developed, which enable the user to experience some of the physical and chemical sensations associated with smoking, without actually generating smoke or fire. As such, these devices are not affected by the restrictions imposed by statutory and other smoking bans.

For example, electronic cigarettes have been developed. These devices resemble a cigarette and are battery-powered electronic devices. Electronic cigarettes typically include, for example, a cigarette-shaped tube and a mouthpiece. The cigarette-shaped tube typically includes a replaceable or refillable liquid cartridge, a heating element, and a power source.

Once the replaceable or refillable liquid cartridge is emptied, it must either be replaced or refilled. Replacing cartridges can be expensive and traditional refilling techniques, such as pouring liquid into the liquid cartridge can be messy and troublesome.

What is needed is an electronic cigarette and an electronic cigarette refilling apparatus that avoids the problems of the prior art.

SUMMARY OF THE INVENTION

The present invention solves some of the problems of the prior art by providing an electronic cigarette and a corresponding electronic cigarette refilling apparatus with the characteristics of a cigarette with reduced adverse health consequences. The electronic cigarette is easily and quickly refilled using the electronic cigarette refilling apparatus. The electronic cigarette refilling apparatus provides: (1) a separate air and liquid passages to prevent the liquid from entering the mouthpiece, (2) an innovative top feeding design to prevent the liquid from returning to the container and contaminating the supply, (3) an innovative sight glass to view the liquid flow, (4) the ability to change out containers quickly and easily, and (5) the ability to refill multiple electronic cigarettes quickly and easily without loss of liquid.

The present invention provides an electronic cigarette having a proximal end and a distal end. The electronic cigarette includes: an atomizer having a proximal end and a distal end, wherein the atomizer includes: a reservoir having a proximal end and distal end, wherein the reservoir includes a liquid including a substance to be vaporized and inhaled by a user; an electrical heating element in physical contact with the reservoir; a cartridge having a proximal end and a distal end, wherein the proximal end of the cartridge is coupled to the distal end of the atomizer, wherein the cartridge includes a power source in electrical communication with the electrical heating element; a mouthpiece having a proximal end and a distal end, wherein the distal end of the mouthpiece is coupled to the proximal end of the atomizer; and a power switch to activate the power source, wherein the power switch is located at the distal end of the cartridge.

In one embodiment, the electronic cigarette further includes an electronic cigarette refilling apparatus having a proximal end and a distal end, wherein the electronic cigarette refilling apparatus includes: a container having a proximal end and a distal end; and a housing having a proximal end, a distal end, a first face, and a second face, wherein the housing includes: a first coupler at the distal end of the housing for receiving the proximal end of the container; a second coupler at the proximal end of the housing for receiving the proximal end of a atomizer in the electronic cigarette; a third coupler at the proximal end of the housing for receiving the distal end of the mouthpiece in the electronic cigarette, wherein the third coupler is opposite the second coupler; a first fluid passage in fluid communication with the first coupler, the second coupler, and the exterior of the proximal end of the housing; and a second fluid passage in fluid communication with the second coupler and the third coupler, wherein the proximal end of the electronic cigarette refilling apparatus is coupled to the distal end of the mouthpiece and further wherein the distal end of the electronic cigarette refilling apparatus is coupled to the proximal end of the atomizer.

In one embodiment, the container includes a bottle. In one embodiment, the bottle is a squeeze bottle. In one embodiment, the squeeze bottle is plastic.

In one embodiment, the housing includes one or more metals, one or more plastics, one or more wooden materials, or a combination thereof.

In one embodiment, the first coupler includes a threaded coupler. In one embodiment, the second coupler includes a retention post coupler fitted with a flexible O-Ring. In one embodiment, the third coupler includes a receptacle coupler.

In one embodiment, the power switch is a push switch. In one embodiment, the electronic cigarette further includes a protective horn surrounding the power switch to prevent accidental activation. In one embodiment, the power source is rechargeable. In one embodiment, the power source is not rechargeable. In one embodiment, the power source includes a disposable battery. In one embodiment, the power source includes a rechargeable battery. In one embodiment, the power source is electrically connected to the electrical heating element. In one embodiment, the power source is sufficient to enable at least about fifty inhalations of the vaporized liquid. In one embodiment, the atomizer is made of one or more metals, one or more plastics, one or more wooden materials, or a combination thereof.

In one embodiment, the cartridge is made of one or more metals, one or more plastics, one or more wooden materials, or a combination thereof.

In one embodiment, the substance includes a pharmacologically active agent. In one embodiment, the pharmacologically active agent is nicotine.

In one embodiment, the electronic cigarette further includes a site-glass on the first face of the housing whereby the user can observe the liquid flow through the first fluid passage when the user applies pressure to outside of the container.

The present invention provides an electronic cigarette having a proximal end and a distal end. The electronic cigarette includes: an atomizer having a proximal end and a distal end, wherein the atomizer includes: a reservoir having a proximal end and distal end, wherein the reservoir includes a liquid including a substance to be vaporized and inhaled by a user;

an electrical heating element in physical contact with the reservoir; a cartridge having a proximal end and a distal end, wherein the proximal end of the cartridge is coupled to the distal end of the atomizer, wherein the cartridge includes a power source in electrical communication with the electrical heating element; and a mouthpiece having a proximal end and a distal end, wherein the distal end of the mouthpiece is coupled to the proximal end of the atomizer; a power switch to activate the power source, wherein the power switch is located at the distal end of the cartridge; and an electronic cigarette refilling apparatus having a proximal end and a distal end, wherein the electronic cigarette refilling apparatus includes: a container having a proximal end and a distal end; and a housing having a proximal end, a distal end, a first face, and a second face, wherein the housing includes: a first coupler at the distal end of the housing for receiving the proximal end of the container; a second coupler at the proximal end of the housing for receiving the proximal end of a atomizer in the electronic cigarette; a third coupler at the proximal end of the housing for receiving the distal end of the mouthpiece in the electronic cigarette, wherein the third coupler is opposite the second coupler; a first fluid passage in fluid communication with the first coupler, the second coupler, and the exterior of the proximal end of the housing; and a second fluid passage in fluid communication with the second coupler and the third coupler, wherein the proximal end of the electronic cigarette refilling apparatus is coupled to the distal end of the mouthpiece and further wherein the distal end of the electronic cigarette refilling apparatus is coupled to the proximal end of the atomizer.

In one embodiment, the electronic cigarette further includes a site-glass on the first face of the housing whereby the user can observe the liquid flow through the first fluid passage when the user applies pressure to outside of the container.

The present invention provides an electronic cigarette having a proximal end and a distal end. The electronic cigarette includes: an atomizer having a proximal end and a distal end, wherein the atomizer includes: a reservoir having a proximal end and distal end, wherein the reservoir includes a liquid including a substance to be vaporized and inhaled by a user, wherein the liquid includes nicotine; an electrical heating element in physical contact with the reservoir; a cartridge having a proximal end and a distal end, wherein the proximal end of the cartridge is coupled to the distal end of the atomizer, wherein the cartridge includes a power source in electrical communication with the electrical heating element; and a mouthpiece having a proximal end and a distal end, wherein the distal end of the mouthpiece is coupled to the proximal end of the atomizer; a power switch to activate the power source, wherein the power switch is located at the distal end of the cartridge; and an electronic cigarette refilling apparatus having a proximal end and a distal end, wherein the electronic cigarette refilling apparatus includes: a container having a proximal end and a distal end; and a housing having a proximal end, a distal end, a first face, and a second face, wherein the housing includes: a first coupler at the distal end of the housing for receiving the proximal end of the container; a second coupler at the proximal end of the housing for receiving the proximal end of a atomizer in the electronic cigarette; a third coupler at the proximal end of the housing for receiving the distal end of the mouthpiece in the electronic cigarette, wherein the third coupler is opposite the second coupler; a first fluid passage in fluid communication with the first coupler, the second coupler, and the exterior of the proximal end of the housing; and a second fluid passage in fluid communication with the second coupler and the third coupler, wherein the proximal end of the electronic cigarette refilling apparatus is coupled to the distal end of the mouthpiece and further wherein the distal end of the electronic cigarette refilling apparatus is coupled to the proximal end of the atomizer, and wherein the power source includes a disposable battery.

The present invention provides an electronic cigarette refilling apparatus to dispense a nicotine-containing liquid into an electronic cigarette. The electronic cigarette refilling apparatus includes: a container having a proximal end and a distal end; and a housing having a proximal end, a distal end, a first face, and a second face, wherein the housing includes: a first coupler at the distal end of the housing for receiving the proximal end of the container; a second coupler at the proximal end of the housing for receiving the proximal end of a atomizer in the electronic cigarette; a third coupler at the proximal end of the housing for receiving the distal end of a mouthpiece in the electronic cigarette, wherein the third coupler is opposite the second coupler; and a first fluid passage in fluid communication with the first coupler, the second coupler, and the exterior of the proximal end of the housing; and a second fluid passage in fluid communication with the second coupler and the third coupler.

The present invention provides an electronic cigarette refilling apparatus to dispense a nicotine-containing liquid into an electronic cigarette. The electronic cigarette refilling apparatus includes: a container having a proximal end and a distal end, wherein the container includes a plastic squeeze bottle; and a housing having a proximal end, a distal end, a first face, and a second face, wherein the housing includes: a first coupler at the distal end of the housing for receiving the proximal end of the container, wherein the first coupler includes a threaded coupler; a second coupler at the proximal end of the housing for receiving the proximal end of a atomizer in the electronic cigarette, wherein the second coupler includes a retention post coupler fitted with a flexible O-Ring; a third coupler at the proximal end of the housing for receiving the distal end of a mouthpiece in the electronic cigarette, wherein the third coupler includes a receptacle coupler, wherein the third coupler is opposite the second coupler; and a first fluid passage in fluid communication with the first coupler, the second coupler, and the exterior of the proximal end of the housing; and a second fluid passage in fluid communication with the second coupler and the third coupler.

In one embodiment, the electronic cigarette refilling apparatus further includes a site-glass on the first face of the housing whereby the user can observe the nicotine-containing liquid flow through the first fluid passage when the user applies pressure to outside of the container.

The present invention provides a method of dispensing a liquid into an electronic cigarette. The method includes: providing an electronic cigarette having a proximal end and a distal end, wherein the electronic cigarette includes: an atomizer having a proximal end and a distal end, wherein the atomizer includes: a reservoir having a proximal end and distal end, wherein the reservoir includes a liquid including a substance to be vaporized and inhaled by a user; an electrical heating element in physical contact with the reservoir; a cartridge having a proximal end and a distal end, wherein the proximal end of the cartridge is coupled to the distal end of the atomizer, wherein the cartridge includes a power source in electrical communication with the electrical heating element; and a mouthpiece having a proximal end and a distal end, wherein the distal end of the mouthpiece is coupled to the proximal end of the atomizer; and a power switch to activate the power source, wherein the power switch is located at the distal end of the cartridge; removing the mouthpiece at the proximal end of the atomizer; inserting a electronic cigarette refilling apparatus having a proximal end and a distal end into the proximal end of the atomizer, wherein the electronic cigarette refilling apparatus includes: a container having a proximal end and a distal end; and a housing having a proximal end, a distal end, a first face, and a second face, wherein the housing includes: a first coupler at the distal end of the housing for receiving the proximal end of the container; a second coupler at the proximal end of the housing for receiving the proximal end of a atomizer in the electronic cigarette; a third coupler at the proximal end of the housing for receiving the distal end of the mouthpiece in the electronic cigarette, wherein the third coupler is opposite the second coupler; a first fluid passage in fluid communication with the first coupler, the second coupler, and the exterior of the proximal end of the housing; a second fluid passage in fluid communication with the second coupler and the third coupler, wherein the proximal end of the electronic cigarette refilling apparatus is coupled to the distal end of the mouthpiece and further wherein the distal end of the electronic cigarette refilling apparatus is coupled to the proximal end of the atomizer, a liquid including nicotine; and injecting the liquid into the atomizer by applying pressure to the container.

In one embodiment, the method further includes removing the electronic cigarette refilling apparatus from the proximal end of the atomizer. In one embodiment, the method further includes inserting the mouthpiece into the proximal end of the atomizer.

The present invention provides a method of inhaling a vapor from an electronic cigarette. The method includes: providing electronic cigarette having a proximal end and a distal end, wherein the electronic cigarette includes: an atomizer having a proximal end and a distal end, wherein the atomizer includes: a reservoir having a proximal end and distal end, wherein the reservoir includes a liquid including a substance to be vaporized and inhaled by a user; an electrical heating element in physical contact with the reservoir; a cartridge having a proximal end and a distal end, wherein the proximal end of the cartridge is coupled to the distal end of the atomizer, wherein the cartridge includes a power source in electrical communication with the electrical heating element; and a mouthpiece having a proximal end and a distal end, wherein the distal end of the mouthpiece is coupled to the proximal end of the atomizer; a power switch to activate the power source, wherein the power switch is located at the distal end of the cartridge; and an electronic cigarette refilling apparatus having a proximal end and a distal end, wherein the electronic cigarette refilling apparatus includes: a container having a proximal end and a distal end; and a housing having a proximal end, a distal end, a first face, and a second face, wherein the housing includes: a first coupler at the distal end of the housing for receiving the proximal end of the container; a second coupler at the proximal end of the housing for receiving the proximal end of a atomizer in the electronic cigarette; a third coupler at the proximal end of the housing for receiving the distal end of the mouthpiece in the electronic cigarette, wherein the third coupler is opposite the second coupler; a first fluid passage in fluid communication with the first coupler, the second coupler, and the exterior of the proximal end of the housing; a second fluid passage in fluid communication with the second coupler and the third coupler, wherein the proximal end of the electronic cigarette refilling apparatus is coupled to the distal end of the mouthpiece and further wherein the distal end of the electronic cigarette refilling apparatus is coupled to the proximal end of the atomizer; activating the power source to provide a vaporized substance; and inhaling the vaporized substance through the mouthpiece.

BRIEF DESCRIPTION OF THE DRAWINGS

Embodiments of the invention may be best understood by referring to the following description and accompanying drawings, which illustrate such embodiments. In the drawings:

FIG. 1 is a side-view drawing illustrating an exemplary electronic cigarette.

FIG. 2 is an exploded side-view drawing illustrating an exemplary electronic cigarette.

FIG. 3 is a top-view drawing illustrating an exemplary electronic cigarette.

FIG. 4 is an exploded top-view drawing illustrating an exemplary electronic cigarette.

Figure 5:
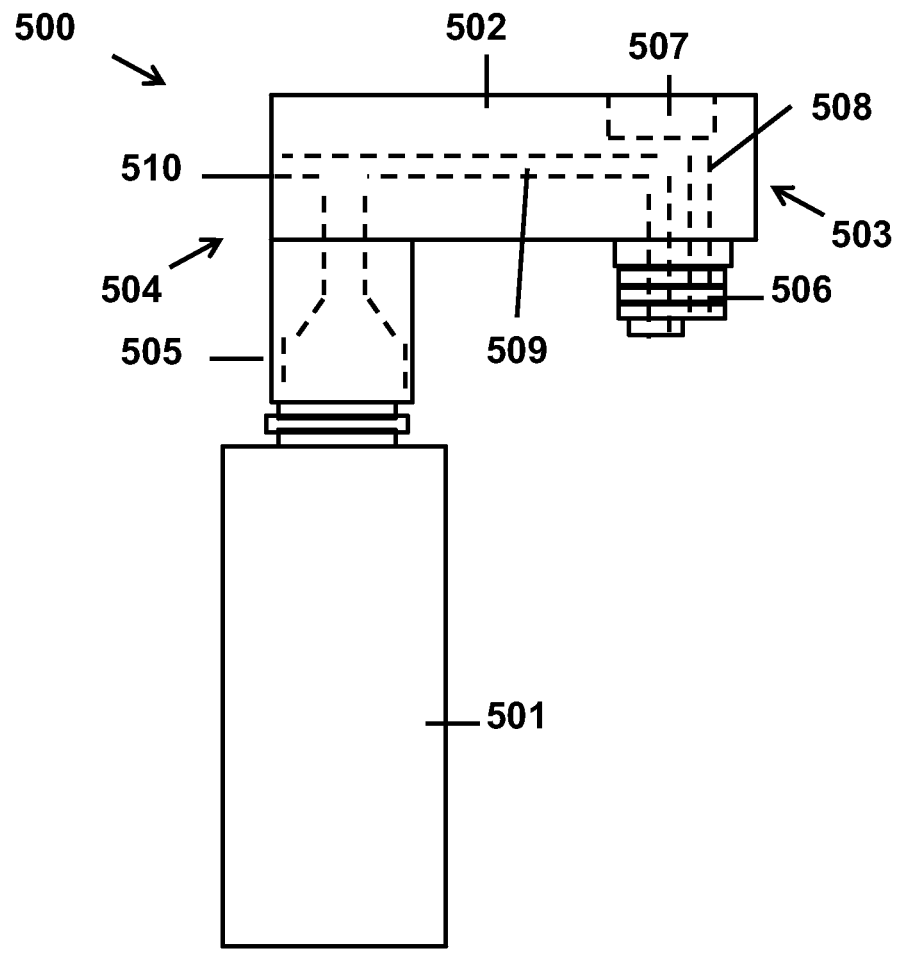
FIG. 5 is a first face-view drawing illustrating an exemplary electronic cigarette refilling apparatus for use with the electronic cigarette.

The drawings are not necessarily to scale. Like numbers used in the figures refer to like components, steps, and the like. However, it will be understood that the use of a number to refer to a component in a given figure is not intended to limit the component in another figure labeled with the same number.

DETAILED DESCRIPTION OF THE INVENTION

The present invention solves some of the problems of the prior art by providing an electronic cigarette and a corresponding electronic cigarette refilling apparatus with the characteristics of a cigarette with reduced adverse health consequences. The electronic cigarette is easily and quickly refilled using the electronic cigarette refilling apparatus. The electronic cigarette refilling apparatus provides: (1) a separate air and liquid passages to prevent the liquid from entering the mouthpiece, (2) an innovative top feeding design to prevent the liquid from returning to the container and contaminating the supply, (3) an innovative sight glass to view the liquid flow, (4) the ability to change out containers quickly and easily, and (5) the ability to refill multiple electronic cigarettes quickly and easily without loss of liquid.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Unless otherwise indicated, the words and phrases presented in this document have their ordinary meanings to one of skill in the art. Such ordinary meanings can be obtained by reference to their use in the art and by reference to general and scientific dictionaries, for example, *Webster's Third New International Dictionary*, Merriam-Webster Inc., Springfield, Mass., 1993 and *The American Heritage Dictionary of the English Language*, Houghton Mifflin, Boston Mass., 1981.

The following explanations of certain terms are meant to be illustrative rather than exhaustive. These terms have their ordinary meanings given by usage in the art and in addition include the following explanations.

As used herein, the term "about" refers to a variation of 10 percent of the value specified; for example about 50 percent carries a variation from 45 to 55 percent.

As used herein, the term "and/or" refers to any one of the items, any combination of the items, or all of the items with which this term is associated.

As used herein, the singular forms "a," "an," and "the" include plural reference unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

As used herein, the term "cigarette" refers to an elongated, rolled tube that contains tobacco or other similar products. A sheet of coiled paper may be used to contain the tobacco. The cigarette has a first end, a second end, and is air permeable. The second end may contain a filter. At least the first end contains tobacco that can be ignited.

As used herein, the term "coupled" refers to the joining of two members directly or indirectly to one another. Such joining may be stationary in nature or movable in nature and/or such joining may allow for the flow of fluids, electricity, electrical signals, or other types of signals or communication between two members. Such joining may be achieved with the two members or the two members and any additional intermediate members being integrally formed as a single unitary body with one another or with the two members or the two members and any additional intermediate members being attached to one another. Such joining may be permanent in nature or alternatively may be removable or releasable in nature.

As used herein, the term "coupler" refers to mechanical element that is used to establish a mechanical connection between two elements. It is preferred that the mechanical connection be mechanically rigid.

As used herein, the terms "include," "for example," "such as," and the like are used illustratively and are not intended to limit the present invention.

As used herein, the term "liquid" refers to a substance that undergoes continuous deformation under a shearing stress. See, e.g., *Concise Chemical and Technical Dictionary*, $4^{th}$ Edition, Chemical Publishing Co., Inc., p. 707, New York, N.Y. (1986).

As used herein, the terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the term "pharmacologically active agent" refers to a chemical compound, complex or composition that exhibits a desirable effect in the biological context, i.e., when administered to a subject. The term includes pharmacologically active, pharmaceutically acceptable derivatives of those active agents specifically mentioned herein, including, but not limited to, salts, esters, amides, prodrugs, active metabolites, isomers, analogs, crystalline forms, hydrates, and the like.

As used herein, the terms "front," "back," "rear," "upper," "lower," "right," and "left" in this description are merely used to identify the various elements as they are oriented in the FIGS, with "front," "back," and "rear" being relative apparatus. These terms are not meant to limit the element which they describe, as the various elements may be oriented differently in various applications.

As used herein, the phrase "smoking a cigarette" refers to heating or combustion of the cigarette to form smoke, which can be drawn through the cigarette. Generally, smoking of a cigarette involves lighting one end of the cigarette and, while the tobacco contained therein undergoes a combustion reaction, drawing the cigarette smoke through the mouth end of the cigarette. The cigarette may also be smoked by other means. For example, the cigarette may be smoked by heating the cigarette and/or heating using an electrical heater.

FIG. 1 is a side-view drawing illustrating an exemplary electronic cigarette 100. The electronic cigarette 100 has a proximal end 101 and a distal end 102. The electronic cigarette 100 includes a mouthpiece 103, an atomizer 104, a cartridge 105, a power switch 106, and a protective horn 107. The distal end of the mouthpiece 103 is coupled to the proximal end of the atomizer 104. The atomizer 104 includes a reservoir (not shown) and an electrical heating element (not shown). The reservoir (not shown) includes the liquid (not shown) to be vaporized by electrical heating element (not shown) and inhaled by the user (not shown) through the mouthpiece 103.

In one embodiment, the liquid includes a pharmacologically active agent. In one embodiment, the pharmacological active agent is nicotine. The liquid may include other materials, for example, one or more organic solvents that may act as a carrier for the pharmacological active agent. For example, the liquid may include nicotine, propylene glycol, optional ingredients, or combinations thereof. The option ingredients may include one or more flavorings, one or more scents, one or more vitamins, and the like, or combinations thereof.

The cartridge 105 includes a power source (not shown) that is in electrical communication with the electrical heating element (not shown) in the atomizer 104.

In one embodiment, the atomizer 104 is a 1.5 Ohm low resistance atomizer.

In one embodiment, the power source is rechargeable. In one embodiment, the power source is not rechargeable. In one embodiment, the power source includes a disposable battery. In one embodiment, the power source includes a rechargeable battery. In one embodiment, the power source is a 3.7 volt rechargeable battery. In one embodiment, the power source includes two 3.0 volt batteries.

The cartridge 105 is coupled to the protective horn 107 and the power switch 106. The power switch 106 may be a push switch. The power switch 106 is coupled to the protective horn 107, which prevents accidental activation.

To operate the electronic cigarette 100, the user (not shown) depresses the power switch 106, which activates the power source (not shown) in electrical communication with the electrical heating element (not shown). As electrical current flows into the electrical heating element (not shown), the internal temperature of the atomizer 104 is increased to a level, which vaporizes the liquid in the reservoir (not shown). Next, the user (not shown) inhales the vaporized liquid through the mouthpiece 103.

The electronic cigarette 100 may be made from many materials, including, for example, one or more metals, one or more plastics, one or more wooden materials, or a combination thereof. In one embodiment, the electronic cigarette 100 is made of stainless steel.

FIG. 2 is an exploded side-view drawing illustrating an exemplary electronic cigarette 200. The electronic cigarette 200 has a proximal end 201 and a distal end 202. The electronic cigarette 200 includes a mouthpiece 203, an atomizer 204, a cartridge 205, a power switch 206, and a protective horn 207. The distal end of the mouthpiece 203 is coupled to the proximal end of the atomizer 204 with coupling 208. The atomizer 204 includes a coupler 209 for coupling with the cartridge 205. The cartridge 205 includes coupler 210, body 211, and spring 212. The power switch 206 is coupled to the protective horn 207 and coupler 213.

To assemble the electronic cigarette 200, the user (not shown) inserts the coupler 208 on the distal end of the mouthpiece 203 into the proximal end of the atomizer 204. The coupler 209 on the distal end of the atomizer 204 is inserted into the coupler 210, which screws into the proximal end of the body 211. The coupler 213, on the proximal end of the protective horn 207 inserts into the spring 212 and screws into the body 211.

FIG. 3 is a top-view drawing illustrating an exemplary electronic cigarette 300. The electronic cigarette 300 has a proximal end 301 and a distal end 302. The electronic cigarette 300 includes a mouthpiece 303, an atomizer 304, a cartridge 305, a power switch 306, and a protective horn 307.

The distal end of the mouthpiece 303 is coupled to the proximal end of the atomizer 304. The atomizer 304 includes a reservoir (not shown) and an electrical heating element (not shown). The reservoir (not shown) includes the liquid (not shown) to be vaporized by electrical heating element (not shown) and inhaled by the user (not shown) through the mouthpiece 303.

FIG. 4 is an exploded top-view drawing illustrating an exemplary electronic cigarette 400. The electronic cigarette 400 has a proximal end 401 and a distal end 402. The electronic cigarette 400 includes a mouthpiece 403, an atomizer 404, a cartridge 405, a power switch 406, and a protective horn 407. The distal end of the mouthpiece 403 is coupled to the proximal end of the atomizer 404 with coupling 408. The atomizer 404 includes a coupler 409 for coupling with the cartridge 405. The cartridge 405 includes coupler 410, body 411, and spring 412. The power switch 406 is coupled to the protective horn 407 and coupler 413.

FIG. 5 is a first face-view drawing illustrating an exemplary electronic cigarette refilling apparatus 500 for use with the electronic cigarette 100. The electronic cigarette refilling apparatus 500 includes a container 501 and a housing 502. The housing 502 has a proximal end 503 and a distal end 504. The housing 502 includes a first coupler 505, a second coupler 506, and a third coupler 507. The first coupler 505 includes a female thread that accepts the male thread on the proximal end of the container 501 to the housing 502. The second coupler 506 includes a male O-ring coupler that accepts the female end of the atomizer (not shown) with the housing 502. The third coupler 507 includes a female coupler that accepts the distal end of the mouthpiece (not shown).

The housing 502 includes two internal fluid passageways 508 and 509. The first fluid passageway 508 provides fluid communication between the exterior of third coupler 507 and the exterior of the second coupler 506.

The second fluid passageway 509 provides fluid communication between the exterior of second coupler 506, the exterior of the first coupler 505, and the pressure release hole 510. The two fluid passageways 508 and 509 prevent inhalation of the liquid prior to vaporization in the atomizer (not shown).

Figure 6:
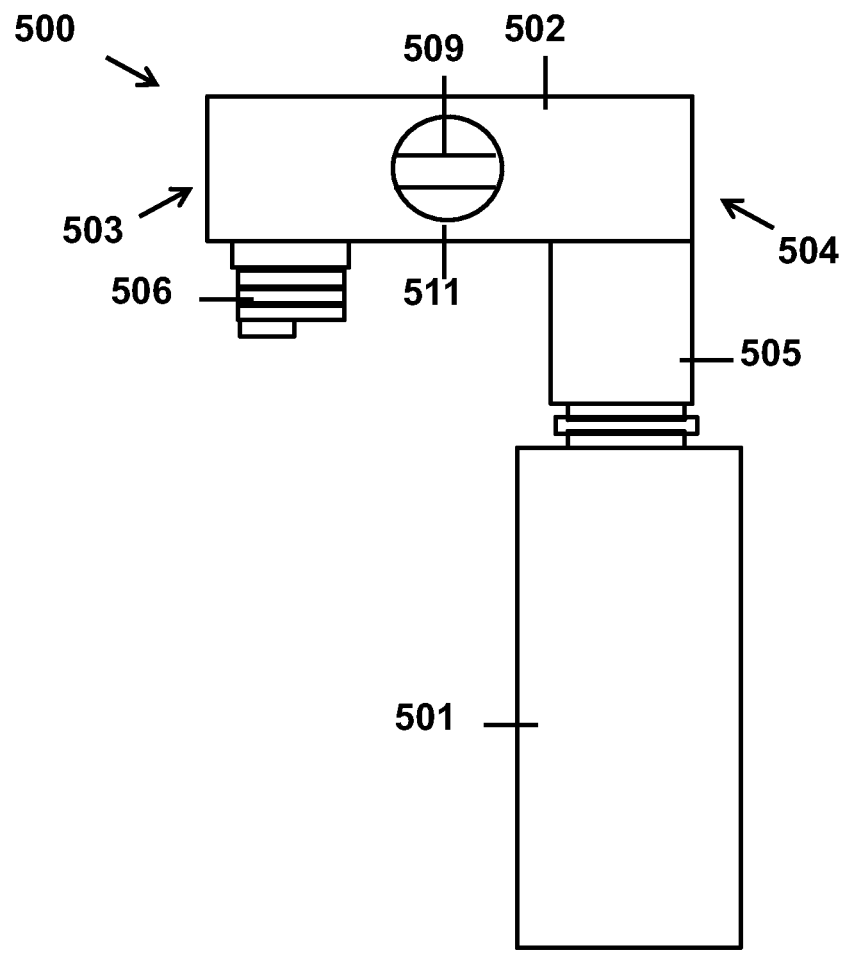
FIG. 6 is a second face-view drawing illustrating an exemplary electronic cigarette refilling apparatus for use with the electronic cigarette.

FIG. 6 is a second face-view drawing illustrating an exemplary electronic cigarette refilling apparatus 500 for use with the electronic cigarette 100. The electronic cigarette refilling apparatus 500 includes a container 501 and a housing 502. The housing 502 has a proximal end 503 and a distal end 504. The housing 502 includes a first coupler 505, a second coupler 506, a third coupler (not shown), and a sight glass 511. The sight glass 511 includes a recession in the housing 502 that includes a clear fluid passageway 509, which enables the user to see the liquid (not shown) flowing through the housing 502 when pressure is applied to the outside to the container 501.

Figure 7:
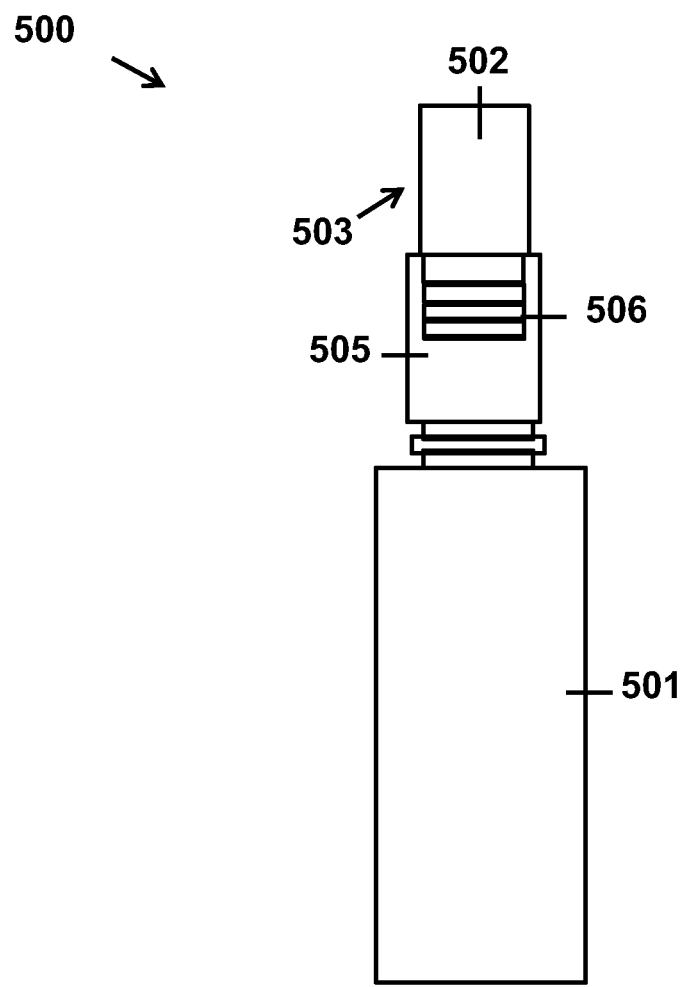
FIG. 7 is a side-view drawing illustrating an exemplary electronic cigarette refilling apparatus for use with the electronic cigarette.

FIG. 7 is a side-view drawing illustrating an exemplary electronic cigarette refilling apparatus 500 for use with the electronic cigarette 100. The electronic cigarette refilling apparatus 500 is shown from the proximal end 503 of the housing 502. The electronic cigarette refilling apparatus 500 includes a container 501 and a housing 502. The housing 502 includes a first coupler 505, a second coupler 506, and a third coupler (not shown).

Figure 8:
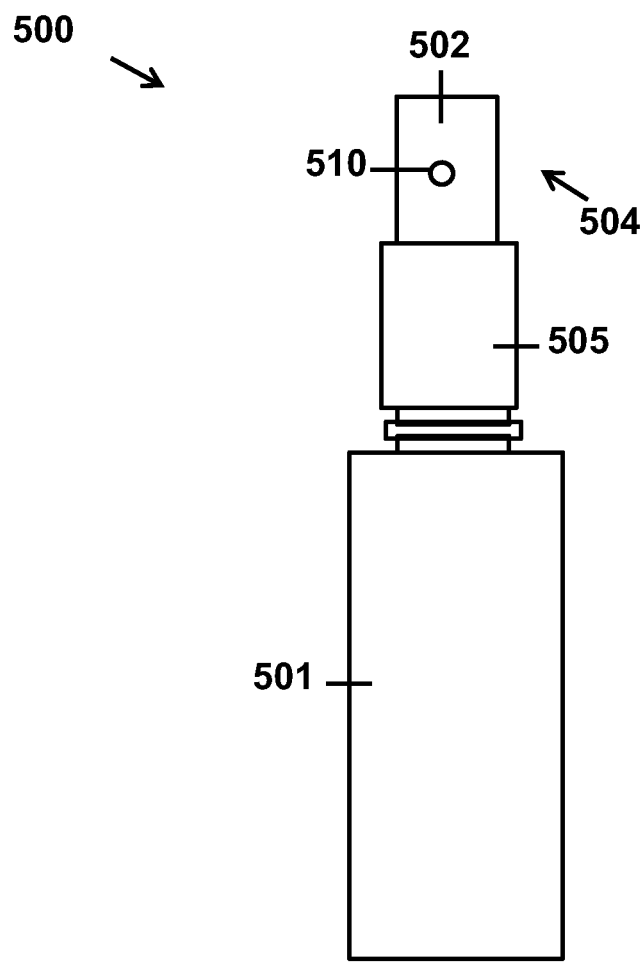
FIG. 8 is a side-view drawing illustrating an exemplary electronic cigarette refilling apparatus for use with the electronic cigarette.

FIG. 8 is a side-view drawing illustrating an exemplary electronic cigarette refilling apparatus 500 for use with the electronic cigarette 100. The electronic cigarette refilling apparatus 500 is shown from the distal end 504 of the housing 502. The electronic cigarette refilling apparatus 500 includes a container 501 and a housing 502. The housing 502 includes a first coupler 505, a second coupler (not shown), a third coupler (not shown), and a pressure release hole 510.

Figure 9:
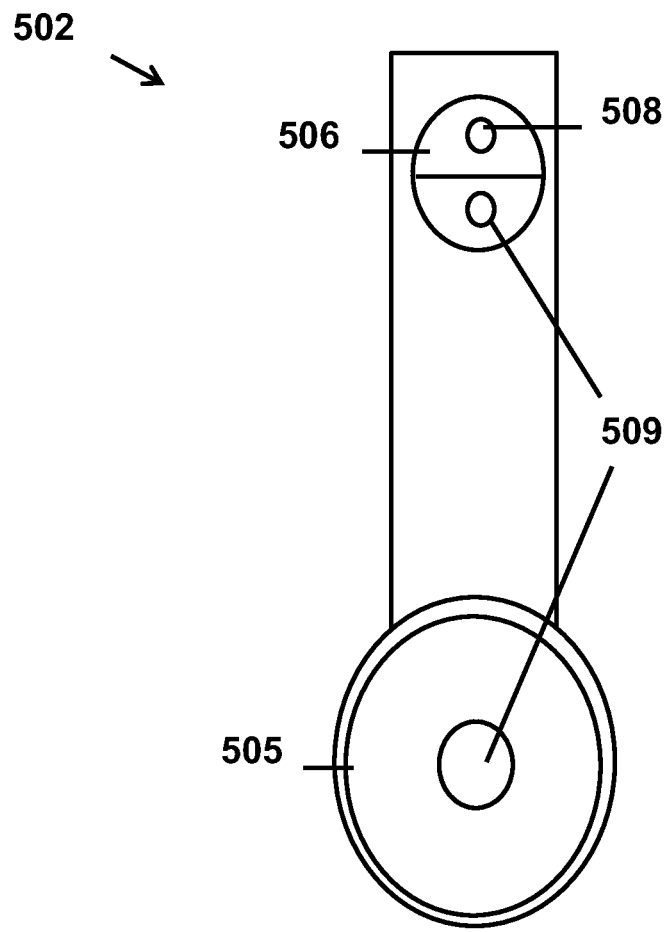
FIG. 9 is a bottom-view drawing illustrating an exemplary housing in an exemplary electronic cigarette refilling apparatus for use with the electronic cigarette.

FIG. 9 is a bottom-view drawing illustrating an exemplary housing 502 for use with the electronic cigarette 100. The housing 502 includes the first coupler 505, the second coupler 506, the first fluid passageway 508, and the second fluid passageway 509.

Figure 10:
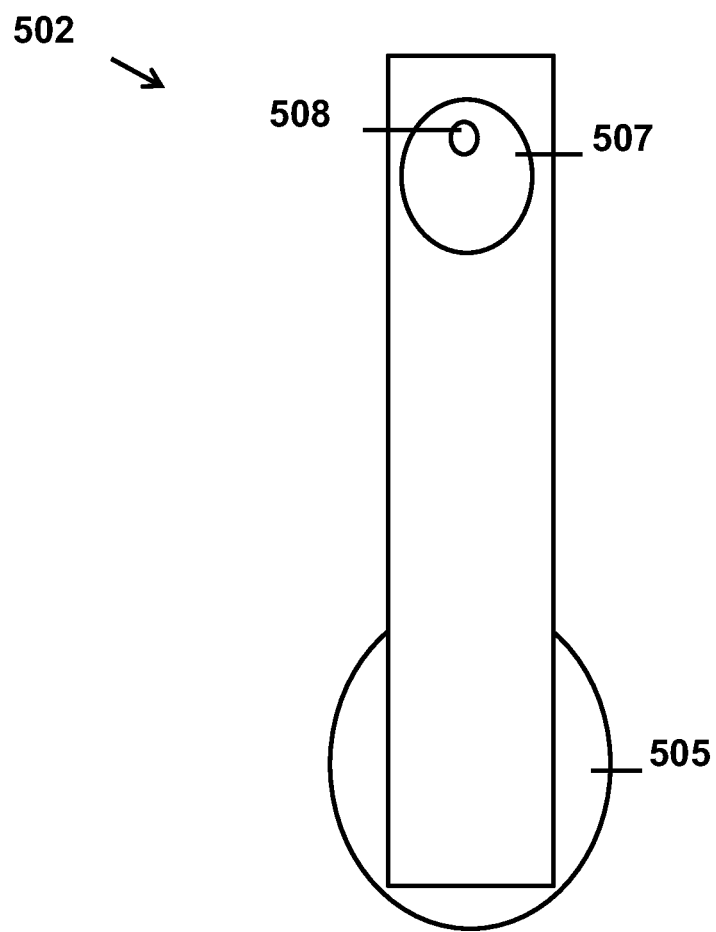
FIG. 10 is a top-view drawing illustrating an exemplary housing in an exemplary electronic cigarette refilling apparatus for use with the electronic cigarette.

FIG. 10 is a top-view drawing illustrating an exemplary housing 502 for use with the electronic cigarette 100. The housing 502 includes the first coupler 505, the third coupler 507, and the first fluid passageway 508.

Figure 11:
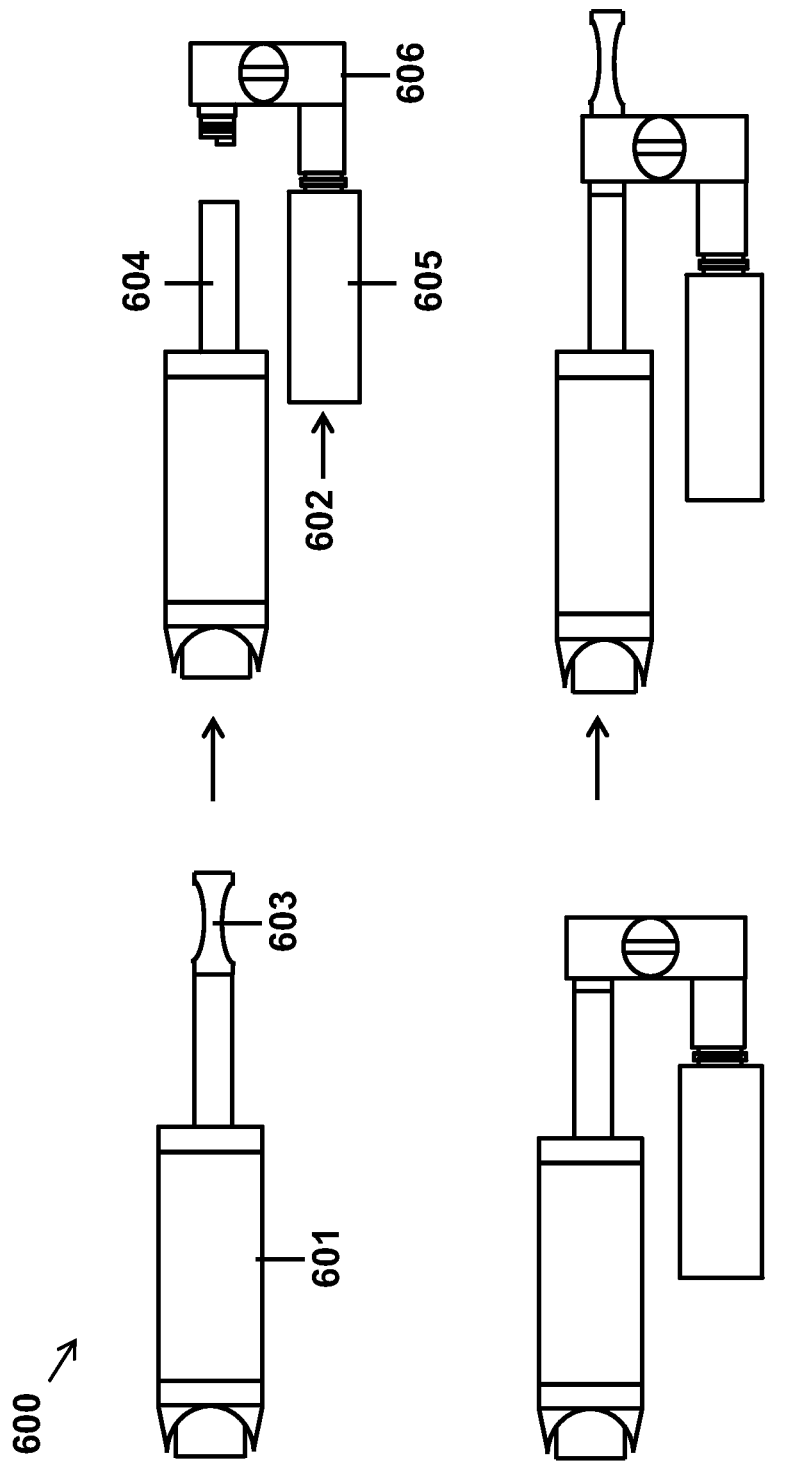
FIG. 11 is side-view drawing illustrating a method of refilling an exemplary electronic cigarette with liquid using an exemplary electronic cigarette refilling apparatus.

FIG. 11 is side-view drawing illustrating a method 600 of refilling an exemplary electronic cigarette 601 with liquid using an exemplary electronic cigarette refilling apparatus 602. First, the mouthpiece 603 is removed from the electronic cigarette 601. Second, the electronic cigarette refilling apparatus 602 is coupled to the atomizer 604 of the electronic cigarette 601. Optionally, the mouthpiece 603 may be inserted into the electronic cigarette refilling apparatus 602 that is coupled with the electronic cigarette 601. Third, pressure is applied to the outside of the container 605 to force liquid from the container 605 through the housing 606 and into the atomizer 604.

Figure 12:
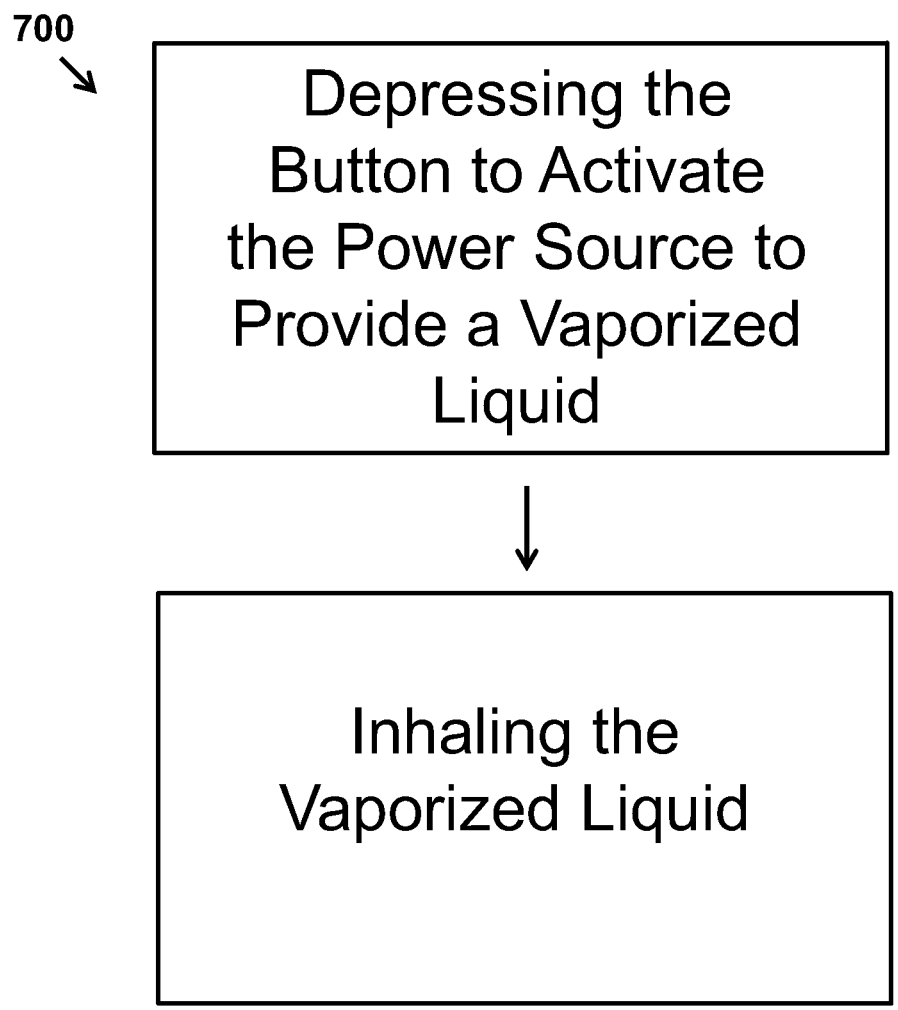
FIG. 12 is a block diagram illustrating a method of inhaling a vapor from an electronic cigarette.

FIG. 12 is a block diagram illustrating a method of inhaling a vapor from an electronic cigarette. The method 700 includes: depressing the push button to activate the power source to provide a vaporized liquid; and inhaling the vaporized substance through the mouthpiece.

Figure 13:
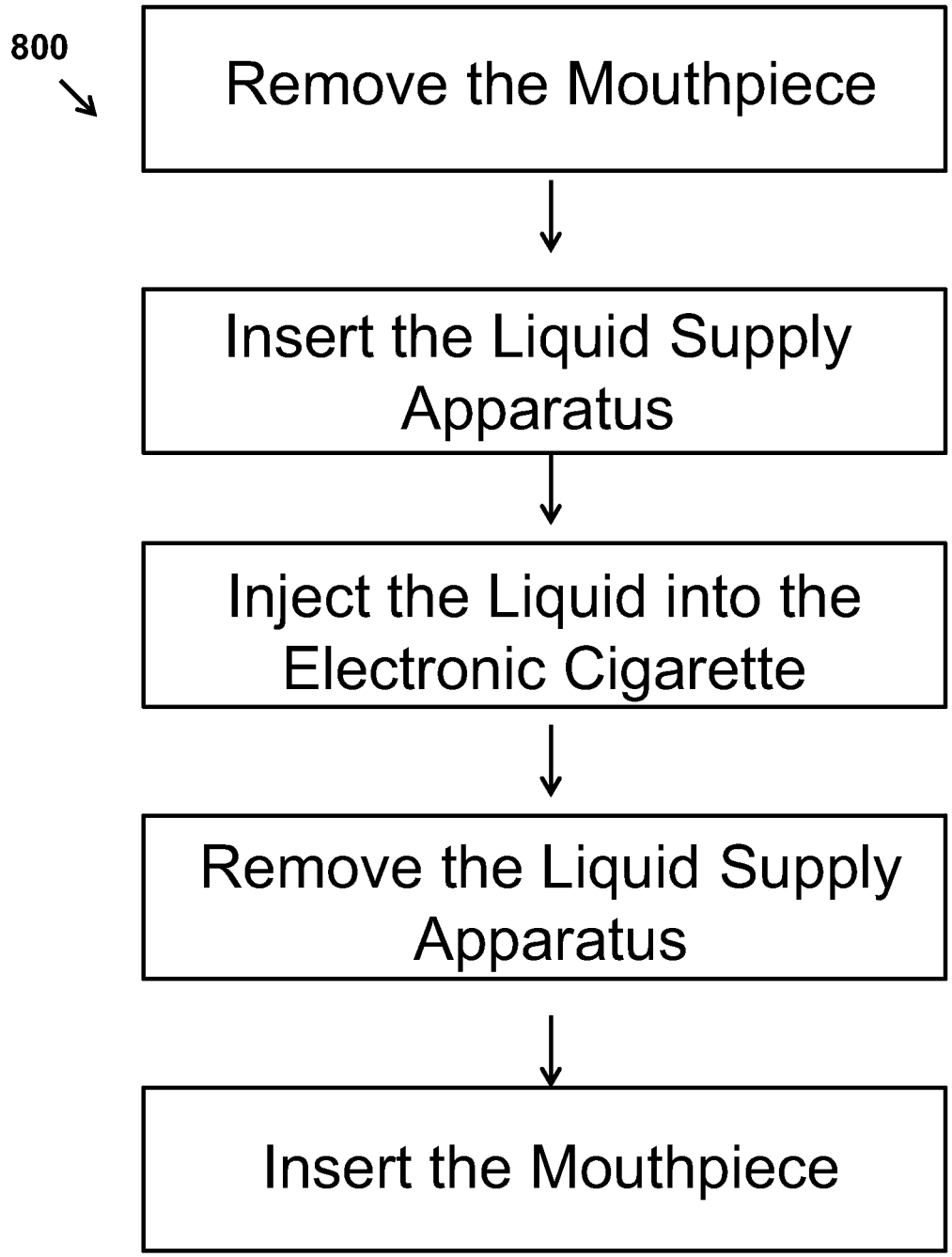
FIG. 13 is a block diagram illustrating a method of refilling an exemplary electronic cigarette.

FIG. 13 is a block diagram illustrating a method 800 of refilling an exemplary electronic cigarette. The method 800 includes: removing the mouthpiece at the proximal end of the atomizer; inserting a electronic cigarette refilling apparatus into the proximal end of the atomizer, injecting the liquid into the atomizer by applying pressure to the container; removing the electronic cigarette refilling apparatus from the proximal end of the atomizer; and inserting the mouthpiece into the proximal end of the atomizer.

In one embodiment, the atomizer is coupled to the cartridge containing a power source with a threaded coupler, typically a seven, eight, or nine millimeter threading. In one embodiment, the mouthpiece is coupled to the atomizer with a friction coupler, which may include an O-Ring retention ring.

In the claims provided herein, the steps specified to be taken in a claimed method or process may be carried out in any order without departing from the principles of the invention, except when a temporal or operational sequence is explicitly defined by claim language. Recitation in a claim to the effect that first a step is performed then several other steps are performed shall be taken to mean that the first step is performed before any of the other steps, but the other steps may be performed in any sequence unless a sequence is further specified within the other steps. For example, claim elements that recite "first A, then B, C, and D, and lastly E" shall be construed to mean step A must be first, step E must be last, but steps B, C, and D may be carried out in any sequence between steps A and E and the process of that sequence will still fall within the four corners of the claim.

Furthermore, in the claims provided herein, specified steps may be carried out concurrently unless explicit claim language requires that they be carried out separately or as parts of different processing operations. For example, a claimed step of doing X and a claimed step of doing Y may be conducted simultaneously within a single operation, and the resulting process will be covered by the claim. Thus, a step of doing X, a step of doing Y, and a step of doing Z may be conducted simultaneously within a single process step, or in two separate process steps, or in three separate process steps, and that process will still fall within the four corners of a claim that recites those three steps.

Similarly, except as explicitly required by claim language, a single substance or component may meet more than a single functional requirement, provided that the single substance fulfills the more than one functional requirement as specified by claim language.

All patents, patent applications, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Additionally, all claims in this application, and all priority applications, including but not limited to original claims, are hereby incorporated in their entirety into, and form a part of, the written description of the invention. Applicants reserve the right to physically incorporate into this specification any and all materials and information from any such patents, applications, publications, scientific articles, web sites, electronically available information, and other referenced materials or documents. Applicants reserve the right to physically incorporate into any part of this document, including any part of the written description, the claims referred to above including but not limited to any original claims.

What is claimed is:

1. A method of dispensing a liquid into an electronic cigarette comprising:
   providing an electronic cigarette having a proximal end and a distal end, wherein the electronic cigarette comprises:
      an atomizer having a proximal end and a distal end, wherein the atomizer comprises:
         a reservoir having a proximal end and distal end, wherein the reservoir comprises a liquid comprising a substance to be vaporized and inhaled by a user;
         an electrical heating element in physical contact with the reservoir;
      a cartridge having a proximal end and a distal end, wherein the proximal end of the cartridge is coupled to the distal end of the atomizer, wherein the cartridge comprises a power source in electrical communication with the electrical heating element; and
      a mouthpiece having a proximal end and a distal end, wherein the distal end of the mouthpiece is coupled to the proximal end of the atomizer; and
      a power switch to activate the power source, wherein the power switch is located at the distal end of the cartridge;
   removing the mouthpiece at the proximal end of the atomizer;
   inserting an electronic cigarette refilling apparatus having a proximal end and a distal end into the proximal end of the atomizer, wherein the electronic cigarette refilling apparatus comprises:
      a container having a proximal end and a distal end; and
      a housing having a proximal end, a distal end, a first face, and a second face, wherein the housing comprises:
         a first coupler at the distal end of the housing for receiving the proximal end of the container;
         a second coupler at the proximal end of the housing for receiving the proximal end of an atomizer in the electronic cigarette;

a third coupler at the proximal end of the housing for receiving the distal end of the mouthpiece in the electronic cigarette, wherein the third coupler is opposite the second coupler;

a first fluid passage in fluid communication with the first coupler, the second coupler, and the exterior of the proximal end of the housing;

a second fluid passage in fluid communication with the second coupler and the third coupler, wherein the proximal end of the electronic cigarette refilling apparatus is coupled to the distal end of the mouthpiece and further wherein the distal end of the electronic cigarette refilling apparatus is coupled to the proximal end of the atomizer, a liquid comprising nicotine; and injecting the liquid into the atomizer by applying pressure to the container.

2. The method of claim 1, further comprising removing the electronic cigarette refilling apparatus from the proximal end of the atomizer.

3. The method of claim 1, further comprising inserting the mouthpiece into the proximal end of the atomizer.

4. An electronic cigarette having a proximal end and a distal end, wherein the electronic cigarette comprises:

an atomizer having a proximal end and a distal end, wherein the atomizer comprises:

a reservoir having a proximal end and distal end, wherein the reservoir comprises a liquid comprising a substance to be vaporized and inhaled by a user;

an electrical heating element in physical contact with the reservoir;

a cartridge having a proximal end and a distal end, wherein the proximal end of the cartridge is coupled to the distal end of the atomizer, wherein the cartridge comprises a power source in electrical communication with the electrical heating element; and a mouthpiece having a proximal end and a distal end, wherein the distal end of the mouthpiece is coupled to the proximal end of the atomizer;

a power switch to activate the power source, wherein the power switch is located at the distal end of the cartridge; and an electronic cigarette refilling apparatus having a proximal end and a distal end, wherein the electronic cigarette refilling apparatus comprises:

a container having a proximal end and a distal end; and a housing having a proximal end, a distal end, a first face, and a second face, wherein the housing comprises:

a first coupler at the distal end of the housing for receiving the proximal end of the container;

a second coupler at the proximal end of the housing for receiving the proximal end of an atomizer in the electronic cigarette;

a third coupler at the proximal end of the housing for receiving the distal end of the mouthpiece in the electronic cigarette, wherein the third coupler is opposite the second coupler;

a first fluid passage in fluid communication with the first coupler, the second coupler, and the exterior of the proximal end of the housing; and a second fluid passage in fluid communication with the second coupler and the third coupler, wherein the proximal end of the electronic cigarette refilling apparatus is coupled to the distal end of the mouthpiece and further wherein the distal end of the electronic cigarette refilling apparatus is coupled to the proximal end of the atomizer.

5. The electronic cigarette of claim 4, wherein the container comprises plastic squeeze bottle.

6. The electronic cigarette of claim 4, wherein the first coupler comprises a threaded coupler.

7. The electronic cigarette of claim 4, wherein the second coupler comprises a retention post coupler fitted with a flexible O-Ring.

8. The electronic cigarette of claim 4, wherein the third coupler comprises a receptacle coupler.

9. The electronic cigarette of claim 4, wherein the power switch is a push switch.

10. The electronic cigarette of claim 4, wherein the power source comprises a disposable battery.

11. The electronic cigarette of claim 4, wherein the substance comprises nicotine.

12. The electronic cigarette of claim 4, further comprising a site-glass on the first face of the housing whereby the user can observe the liquid flow through the first fluid passage when the user applies pressure to outside of the container.

* * * * *